United States Patent [19]

Verstegen

[11] 4,115,208

[45] Sep. 19, 1978

[54] RECOVERY OF STYRENE FROM CRACKED HYDROCARBON FRACTIONS

[75] Inventor: Johannes D. M. Verstegen, Sittard, Netherlands

[73] Assignee: Stamicarbon, B.V., Geleen, Netherlands

[21] Appl. No.: 838,883

[22] Filed: Oct. 3, 1977

Related U.S. Application Data

[63] Continuation-in-part of Ser. No. 716,355, Aug. 20, 1976, abandoned.

[30] Foreign Application Priority Data

Aug. 25, 1975 [NL] Netherlands .......................... 7509991

[51] Int. Cl.² .......................... B01D 3/14; C07C 15/10; C10G 9/44
[52] U.S. Cl. .......................... 203/81; 203/14; 203/87; 208/106; 260/669 A; 260/680 C
[58] Field of Search .......................... 203/24, 26, 81, 74, 203/87, 71, 14, 39, DIG. 19, DIG. 9; 260/669 A, 680 R, 680 C; 208/106

[56] References Cited

U.S. PATENT DOCUMENTS

| | | | |
|---|---|---|---|
| 2,378,067 | 6/1945 | Dorsett et al. | 260/683 R |
| 3,256,355 | 6/1966 | Gilman et al. | 260/669 A |
| 3,654,094 | 4/1972 | Yamagishi et al. | 203/87 |
| 3,684,665 | 8/1972 | Abe et al. | 203/9 |
| 3,689,375 | 9/1972 | Furukawa et al. | 260/669 A |
| 3,763,015 | 10/1973 | Morimoto et al. | 203/9 |

Primary Examiner—Wilbur L. Bascomb, Jr.
Attorney, Agent, or Firm—Cushman, Darby & Cushman

[57] ABSTRACT

A process for recovering maximum amounts of styrene from hydrocarbon fractions produced by thermal cracking of hydrocarbons. The cracked products are subjected to quench cooling and in a separating column separated into a bottom fraction comprised predominantly of hydrocarbons with 9 and more carbon atoms and into a top fraction comprised predominantly of hydrocarbons having less than 9 carbon atoms. The top fraction is fed to a cooling and separating device wherein a cracked gasoline fraction is recovered from which fraction styrene is recovered by fractionation. The cracked gasoline fraction from the separating device can be combined with the hydrocarbon condensates from the first and second compressor stages of a multistage compressor in which the vaporous fraction from the cooling and separating device is compressed.

6 Claims, 2 Drawing Figures

RECOVERY OF STYRENE FROM CRACKED HYDROCARBON FRACTIONS

This invention is a continuation-in-part application of Verstegen, Ser. No. 716,355, filed Aug. 20, 1976 and now abandoned.

The invention relates to a process for recovering styrene from hydrocarbon fractions that contain hydrocarbons with 5 or more carbon atoms said fractions being obtained from cracked products produced in cracking plants for the preparation of α-olefins, particularly ethylene, by the thermal cracking of hydrocarbons.

BACKGROUND OF THE INVENTION

U.S. Pat. Nos. 3,684,665 and 3,763,015 disclose the recovery of styrene from such hydrocarbon fractions. According to the processes disclosed in these references, fractions are recovered from the complex hydrocarbon mixtures by separating lighter hydrocarbons as the top fraction in one column and separating the heavier hydrocarbons as a bottom fraction in the second column. Xylenes and styrene may be separated from these fractions by means of extractive distillation.

Cracking of hydrocarbons for the preparation of ethylene and propylene is a well known process and is effected at a very large scale. Modern cracking plants have capacities for the production of several hundreds of thousands of tons of ethylene per year.

A more detailed general review of various cracking processes is given in report No. 29 'Ethylene' by Shigeyoshi Takaoka of August 1967 and its supplement A report No. 29A 'Ethylene-Propylene' of March 1971 of the Stanford Research Institute; Menlo Part, Calif. These reports discuss several of the more common types of hydrocarbon cracking processes wherein direct heat is used for the cracking. These reports are hereby incorporated by reference.

The Stanford Research Institute reports are merely exemplary. The reaction conditions and the amounts of reaction products and fractions included in the discussion of the flow sheets in the reports will vary depending on the process parameters selected and the composition of the feed streams. The present process while limited to the recovery of styrene from the reaction products of hydrocarbons cracked by direct heating does fall within the overall scope of the disclosure in the Stanford Research reports.

The nature of the starting material which is cracked, the reaction time and the reaction temperature, influence the composition of the cracked products and in particular, the yield of ethylene and propylene. If naphtha is used as a starting material for the cracking process, ethylene yields of 20 to 35% by weight based on the starting material can be obtained at cracking temperatures ranging between 700° to 900° C. Similar yields can also be obtained from other starting materials, including lighter hydrocarbons such as ethane and propane, and from heavier fractions such as kerosene or gas oil, by choosing the appropriate process conditions.

Ethylene and propylene are not the only products of these cracking processes. Various other hydrocarbons, such as methane, ethane, propane, butenes and butanes, fractions consisting of hydrocarbons with at least 5 carbon atoms and having a maximum boiling point ranging between 180° to 250° C., the so-called cracked gasoline, and the heavier fraction, the quench oil, are produced. In addition, the reaction mixture from the cracking plant also contains slight amounts of hydrogen. Generally, both the quench oil and the cracked gasoline contain aromatic compounds. In most cracking processes, the amounts of ethane produced are so large, that after separation of other components, the ethane component is recycled to the furnace or to a separate ethane cracker to be employed as a material to be cracked.

DESCRIPTION OF THE INVENTION

Steam is added to a hydrocarbon feed, which is to be cracked by a direct heating process, in order to reduce the partial pressure of the hydrocarbons, to shorten the residence time and to prevent carbon deposits in the furnace tubes by reaction of the steam with carbon to form carbon oxides and hydrogen. The reaction mixture from the cracking furnaces, which consequently also contains steam, is quenched in order to prevent reduction of the yields of ethylene and propylene due to secondary reactions.

The reaction products which have been quenched to temperatures of about 220° C. are then passed into a first separating column, in which quench oil as a liquid bottom fraction is separated from the lighter hydrocarbons and steam which form the gaseous top fraction. The quench oil in addition to saturated aliphatic hydrocarbons, also contains cyclic compounds such as naphthenes and aromatic compounds and unsaturated hydrocarbons such as olefins, dienes, acetylene derivatives and the like. It is generally quite difficult to separate any particular component from the quench oil and to refine that component.

In cracking plants, the temperature and the pressure in the first separating column are usually chosen so that the quench oil fraction will be in general, comprised predominantly of hydrocarbons with 9 or more carbon atoms. The hydrocarbon portion of the gaseous top fraction is comprises predominantly of hydrocarbons of less than 9 carbon atoms. The fractionating efficiency of the first column is generally not particularly high; thus sharp separation is not usually effected. While the lighter fraction contains heavy hydrocarbons, the heavy fraction also contains components of the lighter fraction. This phenomenon does not particularly affect the essence of the invention.

The gaseous top fraction is passed to a cooling device where a part of the hydrocarbons contained therein and a part of the water vapor are condensed forming a water/hydrocarbon condensate. The water/hydrocarbon condensate and the uncondensed portion comprised of water/hydrocarbon vapor mixture are then passed to a second separating device, where the water is separated from the water/hydrocarbon condensate to form a dehydrated hydrocarbon condensate. This separating device may be designed so that there is also some separation of the dehydrated hydrocarbon condensate into a so-called heavy cracked gasoline and a so-called cracked gasoline of a final boiling point of 180° to 250° C.

In addition to liquid fractions, the uncondensed water/hydrocarbon vapor mixture is also separated out by the second separating device.

The heavy cracked-gasoline from the second separation device is returned to the first separating column. The water, after stripping of minor quantities of hydrocarbons, is generally returned to the cracking plant to be recycled as steam to be used in the initial cracking step.

Usually, said uncondensed water/hydrocarbon vapor mixture from the second separating device is compressed to about 30 atmospheres in a multistage compressor. After each compression stage, the compressed mixture is cooled to remove the heat of compression, causing partial condensation. After both the first and second compression stages, which are conducted at pressures of up to about 5 atmospheres, water/hydrocarbon condensates are obtained which contains relatively large portions of hydrocarbons of 5 to 8 carbon atoms. In the subsequent compression stages, a vapor comprised mainly of hydrocarbons of 1 to 4 carbon atoms and also containing hydrogen is compressed. Mainly ethylene is recovered from the compressed gas of the final compression stage, which is rich in hydrocarbons of 1 to 4 carbon atoms. Propylene and butylene may also be recovered from this gas mixture.

It is common practice to combine the cracked gasoline fraction which is obtained after cooling and separation of the aforementioned top fraction from the first separating column with the dry hydrocarbon condensates from all of the various compression stages. Cracked gasoline obtained in this manner has a high octane number due to the relatively large amount of aromatic compounds contained therein, and thus, is often mixed with motor fuel to increase its octane number. Although the aromatic content of the cracked gasoline is high for motor fuel, it is too low for an economic recovery of pure aromatic, especially styrene. Thus, the recovery of styrene, in accordance with processes described in U.S. Pat. Nos. 3,684,665 and 3,763,015, is not economically attractive.

It has been found that the water/hydrocarbon condensates from the third and following compression stages, and the condensate of the cooled final gas are substantially free of styrene and other aromatic compounds with 8 carbon atoms.

The invention is directed to a process for recovering styrene from a hydrocarbon fraction, the so-called cracked gasoline, which contains hydrocarbons of 5 or more carbon atoms and has a maximum boiling point ranging between 180° to 250° C. These hydrocarbon fractions result from products of cracking plants in which α-olefins, particularly ethylene, are produced by the thermal cracking of hydrocarbons. The process is characterized by recovering styrene from cracked gasoline fractions obtained from a separating device that has been fed with the cooled top products from a separating column. In the separating column, the quenched reaction mixture from the cracking plant is separated into a bottom fraction of a so-called quench oil, comprised predominantly of hydrocarbons of 9 or more carbon atoms and into a top fraction of cracked gasoline, comprised predominantly of hydrocarbons of 5 to 9 carbon atoms and lighter hydrocarbons.

The water/hydrocarbon vapor mixture from the second separating device is compressed to about 30 atmospheres in a multistage compressor. After each compression stage, the compressed mixture is cooled to remove the heat of compression which causes partial condensation which forms a second water/hydrocarbon condensate and a second uncondensed water/hydrocarbon vapor mixture. Said condensate is then removed from said vapor mixture. The second uncondensed water/hydrocarbon vapor mixtures are then subjected to the subsequent sequential compression stages. The water is separated from the second water/hydrocarbon condensates to form a plurality of dehydrated condensates. After both the first and second compression stages which are conducted at pressures up to about 5 atmospheres, the water/hydrocarbon condensate obtained may contain relatively large portions of hydrocarbons of 5 to 8 carbon atoms.

It has been discovered that the water/hydrocarbon condensates from the first and second compression stages of a multistage compressor, may contain rather considerable amounts of styrene. Whether these condensates contain rather considerable amounts of styrene or not depend on the composition of the hydrocarbon feed, e.g., naphtha, the process conditions and the compression ratio's. Thus, in order to increase the total yield of styrene, cracked gasoline recovered from the first separating column may be fixed either with the dehydrated hydrocarbon condensates from the first or from the first and second compression stages. The amount of said condensates as compared to the amount of cracked gasoline recovered from the first separating column can vary widely. If the amount of dehydrated hydrocarbon condensate is relatively small, e.g., less than 20% of the cracked gasoline, or even less than 10%, it may not be worthwhile to combine the condensate with the cracked gasoline. Although the styrene content in a mixture of the cracked gasoline and the dehydrated hydrocarbon condensate of the first and optionally the second compression stage is generally somewhat lower than that in the cracked gasoline recovered from the first separating column, the amount of styrene in the dehydrated hydrocarbon condensates from the first and second compression stages may be high enough, that the yield of recovery in accordance with the process is fully justified economically.

The styrene content of the ultimate fraction from which styrene is isolated ranges from 8 to 14% by weight which is considerably higher than the usual amounts of 3 to 6% by weight of styrene recovered from the combined cracked gasoline fractions in accordance with the art. In accordance with the invention, styrene can be separated effectively and profitably from hydrocarbon cracking plants and even competitively when compared to processes for the preparation of synthesizing styrene.

DESCRIPTION OF THE DRAWINGS

By way of example the invention will be illustrated by reference to the drawings.

For simplification, parts of the cracking process and the treatment of the cracked products are shown only in one of the figures. The cracking section is shown only in FIG. 1. Only the first two stages of the compression section are shown in FIG. 1 with the whole compression section, being shown only in FIG. 2.

Temperatures and pressures which are mentioned are given by way of example. As it is well known in the art, the embodiments described above, may be varied on a technical scale while basic principles remain the same.

Figure 1:
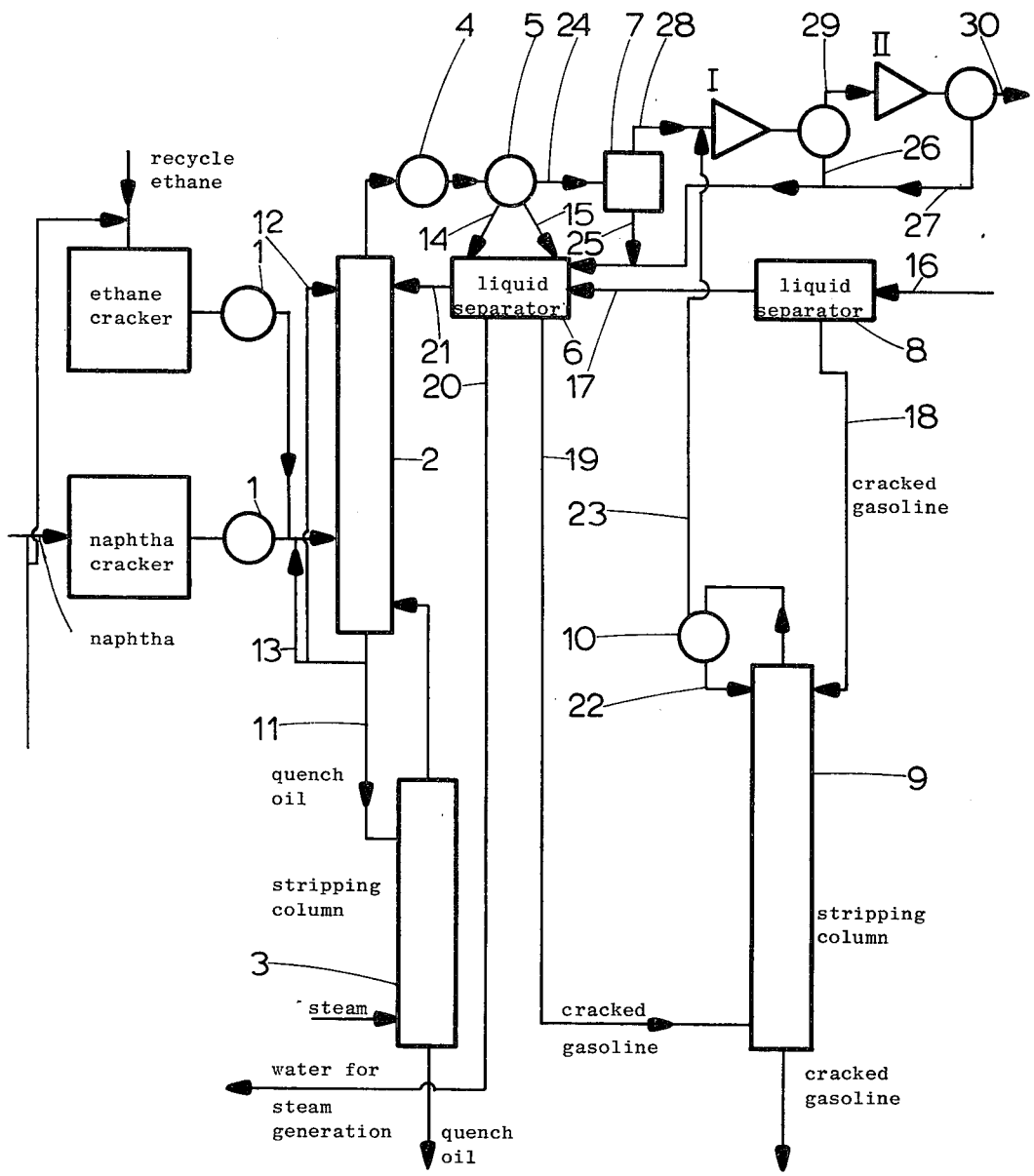
FIG. 1 is directed to a schematic representation of cracking process undertaken in accordance with the prior art.

In FIG. 1, naphtha, to which steam is added, is fed to the naphtha cracking installation. Ethane that is recovered from the cracked products, is recycled to the ethane cracker. Steam is also added to the recycle ethane.

The cracked products from the naphtha and the ethane crackers are quenched (cooled) in quench-coolers 1 and then passed into the first separating column 2. The bottom fraction of this column, being called quench oil is in part 12 returned to the top of column 2, and in part 13 returned as feed in the flow of cracked products to column 2, whereas another part 11 is passed to stripping column 3, where the light fractions are steam-stripped from the quench oil. The bottom fraction of column 3, being quench oil free from light fractions is discharged. The top fraction from stripping column 3 is returned to the separating column 2. The vaporous top fraction of column 2 is cooled 4, whereupon it is partly condensed and then passed into a liquid-separating device 5 which is connected to the liquid separator 6. In this embodiment the liquid hydrocarbons are separated in separating device 5 into cracked gasoline 15 and heavy cracked gasoline 14, and, these hydrocarbon fractions are separated in the liquid separator 6, from the water which entered the process as steam 20, which is then used as process water for the preparation of steam for the cracking plant. The heavy cracked gasoline 21 is returned to the first separating column 2. Flow 24 from the separating device 5 contains not only hydrocarbons of 1 to 4 carbon atoms, but also hydrocarbons of 5 to 9 or 10 carbon atoms and water vapor. After a liquid-vapor separator 7, where water/hydrocarbon condensate droplets are separated and returned 25 to the liquid separator 6, the uncondensed water/hydrocarbon vapor mixture is passed 28 to the first compressor I, where a compression to about 2.8 atm. is effected, followed by cooling and separating the water/hydrocarbon condensate 26 and the uncondensed water/hydrocarbon vapor mixture 29. The condensate 26 is combined with a similar condensate 27 from the second compression stage and then with the liquid fraction from the separator 7 and recycled to separator 6. The uncondensed water/hydrocarbon vapor mixture 29 is passed to the second compression stage (II) and then cooled and separated into a water/hydrocarbon condensate 27 and an uncondensed water/hydrocarbon vapor mixture 30. The uncondensed water/hydrocarbon vapor mixture is compressed further to a final absolute pressure of about 30 atm. The water/hydrocarbon condensates that are formed in cooling the compressed products of the third, fourth and fifth compression stage (32, 34 and 37, FIG. 2) are combined and recycled through 16 to separator 8. After the cooling after the fourth compression stage, the vaporous constituents 35 are washed in two columns (see FIG. 2) to remove sulphur compounds and other acid compounds. The water/hydrocarbon condensates (32, 34 and 37, FIG. 2) after the compression stage III, IV, and V are combined and recycled to the liquid separator 8 as a joint flow 16. Water 17 is returned from said separator 8 to separator 6. The hydrocarbon condensate 18 is passed to stripping column 9. Volatile components are returned from separator 8 through conduit 38 to the compression line after the fourth stage. The cracked gasoline fraction 19 from the liquid separator 6 is also passed to stripping column 9, being provided with a refluxer 10, from which a part of the top fraction is returned through conduit 22 to said stripping column and the remaining part 23 is passed to the first compression stage.

The cracked gasoline, that is obtained as bottom fraction from column 9 contains 3 to 6% of styrene. Because of the comparatively high content of aromatics, this cracked gasoline is processed as a component for motor fuel, often after selective hydrogenation. It is also possible first to extract benzene from the cracked gasoline and then to use the remainder as a component for motor fuel. The content of aromatics in this cracked gasoline is too low to enable the styrene recovery to be effected profitably.

Figure 2:
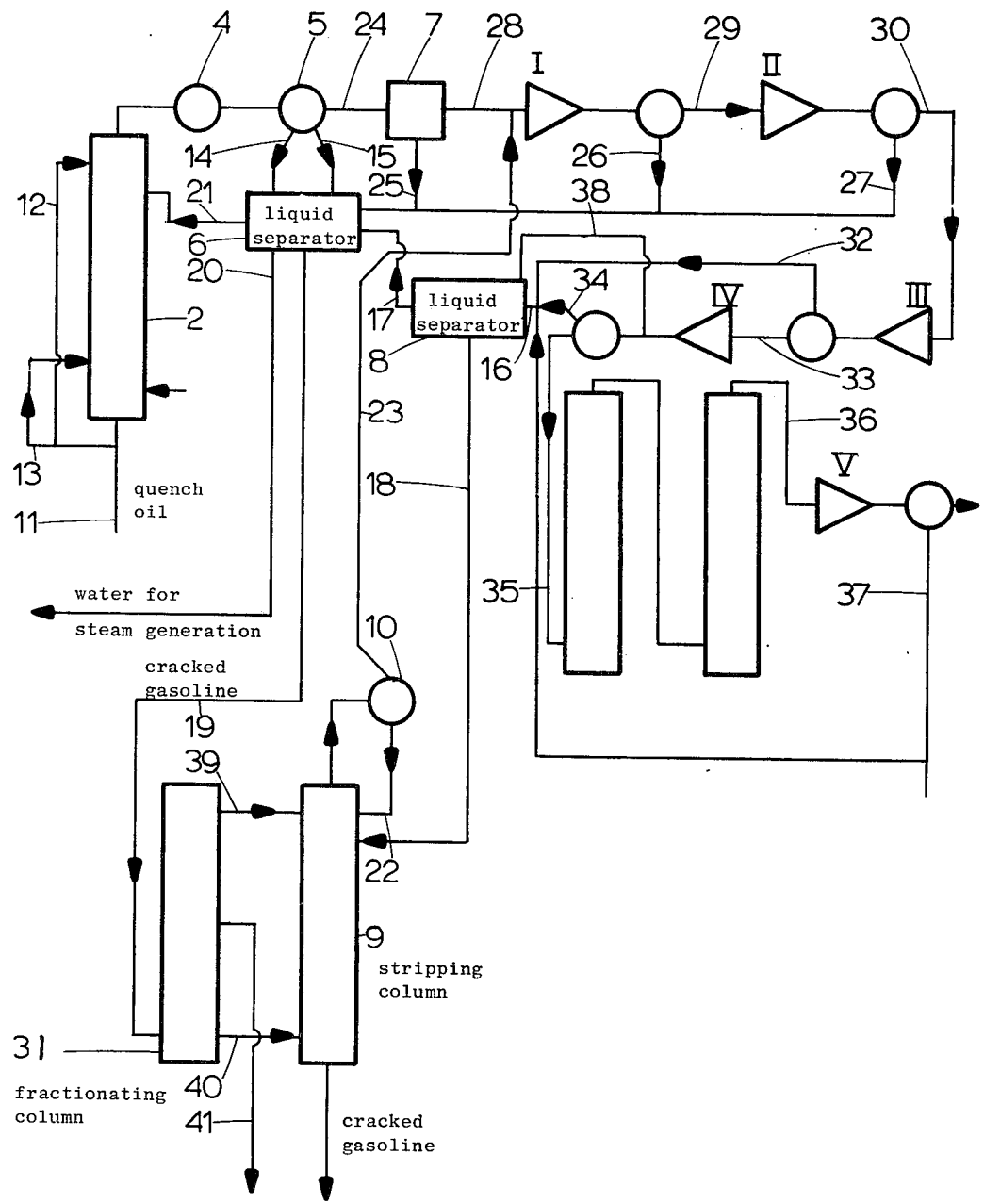
FIG. 2 is directed to the improvement of the invention.

In FIG. 2, in an embodiment of the process according to the invention, flow 19 is passed, first to a fractionating column 31, instead of to column 9. Out of column 31 three fractions are obtained, viz, a fraction with hydrocarbons with at most 5, preferably at most 7 carbon atoms 39 a fraction with hydrocarbons with more than 9 carbon atoms 40, and a fraction largely consisting of hydrocarbons with 8 carbon atoms 41, of which styrene and xylenes form a considerable part. The first-mentioned two fractions may be passed, e.g., into column 9 (as shown in FIG. 2), but, naturally, this is not necessary. Styrene can then be recovered, in a manner known per se, from the fraction containing styrene and xylenes (flow 41 in FIG. 2).

The amount of combined flows 25, 26 and 27 may differ greatly from that of flow 15, which depends, i.e., on the process control. Said combined flows may be less than 10% by weight of flow 15 and have a styrene content of only 6-8%. Mixing said combined flow 25, 26 and 27 with 15 in separator 6 to form flow 19 will then offer little advantage, but also little disadvantage. If the amount of the combined flows 25, 26 and 27 is considerable with respect to flow 15, but said combined flows contain little styrene, combination with 15 in separator 6 to form flow 19 will seriously affect the economy of the styrene recovery, and it will then generally be more advantageous to pass the liquid flow from separator 7 to separator 6, and to pass the liquid flows from the coolers after the compressors I and II to separator 8 together with 32, 34 and 37.

In general, the amount of the combined flows 25, 26 and 27 is of the same order as flow 15 or even greater, and the styrene content is such that a flow 19 with a styrene content of 8-14% by weight is obtained from separator 6. Recovery of styrene from this flow is possible in a highly profitable way.

In an embodiment used by applicant, the combined flows 25, 26 and 27 are about as large as flow 15. Flow 15 contains 12-14% by weight of styrene, said combined flows 8-10% by weight, and flow 19 10-12% by weight.

Flow 18 which does not contain recoverable amounts of styrene or xylenes is about twice as large as flow 19, so that, if 18 should be mixed with 19, the styrene content in the combined flow would be reduced to ⅓ of the styrene content in flow 19, i.e., to 3-4% by weight.

Various modifications of the process of the invention may be made without departing from the spirit or scope thereof and it should be understood that the invention is intended to be limited only as defined in the appended claims.

What is claimed is:

1. In a process for recovering styrene from the reaction products of the thermal cracking of hydrocarbons wherein hydrocarbons mixed with steam are directly heated and cracked, which process comprises the steps of,
   (1) quenching and fractionating the reaction products into a liquid bottom fraction comprises predominantly of hydrocarbons with nine or more carbon atoms and a vaporous top fraction comprised predominantly of hydrocarbons with less than 9 carbon atoms and water vapor, (2) cooling said vaporous top fraction to form a condensed portion comprised of water/hydrocarbon condensate, and an uncondensed portion comprised of water/hydrocarbon vapor mixture, (3) subjecting the said vapor mixture to a multistage compression, wherein immediately after each compression stage the compressed products are cooled and in part condensed to form a plurality of second water/hydrocarbon condensates and a plurality of second uncondensed water/hydrocarbon vapor mixtures, said last mentioned vapor mixtures are respectively separated from said second condensate and subjected to the subsequent sequential compression stages, (4) separating the water from the plurality of said second water/hydrocarbon condensates obtained in step (3) to form a plurality of dehydrated hydrocarbon condensates and passing said dehydrated hydrocarbon condensates to a stripping column, (5) removing the water from the water/hydrocarbon condensate of step (2) to form a dehydrated hydrocarbon condensate, (6) passing said dehydrated hydrocarbon condensate of step (5) to the stripping column of step (4), and (7) stripping said dehydrated hydrocarbon condensates of steps (4) and (5) in said stripping column, the improvement consisting essentially of the combination of the additional steps prior to any introduction of said dehydrated hydrocarbon condensate obtained in step (5)

(A) passing said dehydrated hydrocarbon condensate of step (5) to a fractionating column and fractionating said dehydrated hydrocarbon condensate of step (5), whereby there is separately obtained:

(i) a first fraction having 8-carbon-atom hydrocarbons, (ii) a second fraction having less-than-8-carbon-atom hydrocarbons, and (iii) a third fraction having more-than-8-carbon atom hydrocarbons, (B) thereafter recovering styrene from said first (i) fraction.

2. The process of claim 1, wherein the dehydrated hydrocarbon condensate recovered from the first stage of the multistage compression of step (3) is passed to the fractionating column of step (A) and fractionated therein.

3. The process of claim 1, wherein the dehydrated hydrocarbon condensates recovered from the first and second stages of the multistage compression of step (3) are also passed to the fractionating column of step (A) and fractionated therein.

4. The process of claim 1, wherein the second and third fractions (ii) and (iii) of step (A) are passed to the stripping column of step (4) and stripped therein.

5. The process of claim 4, wherein the dehydrated hydrocarbon condensate recovered from the first stage of the multistage compression of step (3) is also passed to the fractionating column of step (A) and fractionated therein.

6. The process of claim 4, wherein the dehydrated hydrocarbon condensates recovered from the first and second stages of the multistage compression of step (3) are also passed to the fractionating column of step (A) and fractionated therein.

* * * * *